United States Patent [19]
Haas et al.

[11] Patent Number: 5,817,870
[45] Date of Patent: Oct. 6, 1998

[54] PROCESS FOR THE PRODUCTION OF MALONIC ACID OR A SALT THEREOF

[75] Inventors: Thomas Haas, Frankfurt; Martin Meier, Werl; Christoph Brossmer, Frankfurt; Dietrich Arntz, Oberursel; Andreas Freund, Kleinostheim, all of Germany

[73] Assignee: Degussa Aktiengesellschaft, Frankfurt, Germany

[21] Appl. No.: 897,139

[22] Filed: Jul. 21, 1997

[30] Foreign Application Priority Data

Jul. 20, 1996 [DE] Germany ............... 196 29 372.3

[51] Int. Cl.⁶ .................... C07C 51/235; C07C 55/08
[52] U.S. Cl. ............................ 562/531; 562/590
[58] Field of Search ........................ 562/531, 590

[56] References Cited

U.S. PATENT DOCUMENTS 2,006,314  6/1935  Halbig et al. ................. 562/531
4,959,494  9/1990  Felthouse ................. 562/515

FOREIGN PATENT DOCUMENTS 54-075823   6/1979   Japan .
55-167246  12/1980   Japan .
57-042650   3/1982   Japan .

*Primary Examiner*—Paul J. Killos
*Assistant Examiner*—Rosalynd Keys
*Attorney, Agent, or Firm*—Wenderoth, Lind & Ponack, L.L.P.

[57] ABSTRACT

Malonic acid or a salt of the same is obtained at high yield according to the invention through the catalytic oxidation with oxygen or an $O_2$-containing gas of 3-hydroxy propionaldehyde or 3-hydroxy propionic acid in the aqueous phase. The conversion takes place in the presence of at least 10 percent by weight, relative to the $C_3$ building block used, of a precious metal from the platinum group. Pd and Pt supported catalysts are preferred.

12 Claims, No Drawings

PROCESS FOR THE PRODUCTION OF MALONIC ACID OR A SALT THEREOF

SPECIFICATION

The invention is directed toward a process for the production of malonic acid or a salt thereof, which is based on the catalytic oxidation of a $C_3$ starting material with oxygen or an oxygen-containing gas in the presence of a precious metal. According to the invention 3-hydroxy propionaldehyde or 3-hydroxy propionic acid or a water-soluble salt of the same is used as the $C_3$ starting material.

BACKGROUND OF THE INVENTION

Malonic acid as well as its water-soluble salts are valuable synthetic intermediates. Malonic acid is conventionally produced from chloroacetic acid and sodium cyanide or from a chloroacetic acid ester and carbon monoxide. Both processes are rather complicated and require the use of toxic starting materials (Ullmann's Enzyklopedie der technischen Chemie, 4th Edition (1978), Vol. 16, pp 415 and Kirk-Othmer Encyclopedia of Chemical Technology. 4th Edition, Vol. 15, pp. 932–933). These disadvantages can be avoided if 1,3-propanediol is oxidized to malonic acid in the presence of a platinum-group catalyst with oxygen or an oxygen-containing gas—see JP-A 56/5433 and DE-A 41 07 986. While in the process of the JP document, in the presence of 3.3 percent by weight of palladium, relative to the diol, malonic acid can be obtained in a yield of 84%, in the process of the DE document using a smaller quantity of catalyst the reaction time could be shortened. However, additionally an adaptation stage of the catalyst is required.

DESCRIPTION OF THE INVENTION

The object of the present invention comprises a further process for the production of malonic acid or a salt thereof through the catalytic oxidation of a $C_3$ starting material leading to a high yield.

Accordingly, a process was found for the production of malonic acid or a salt thereof comprising the catalytic oxidation of a $C_3$ starting material with oxygen or an oxygen-containing gas in the presence of a catalyst comprising a precious metal from the platinum group in the aqueous phase at a pH-value of equal to or greater than 6 and isolation of the malonic acid or a salt of the same from the reaction mixture, characterized in that as the $C_3$ starting material there is used 3-hydroxy propionaldehyde or 3-hydroxy propionic acid or a water-soluble salt of the same, and the catalyst is used in a quantity corresponding to at least 10 percent by weight of the precious metal relative to the $C_3$ starting material.

Preferred embodiments of the process according to the invention are disclosed.

$C_3$ starting materials in the process according to the invention are either 3-hydroxy propionaldehyde or 3-hydroxy propionic acid or a water-soluble salt thereof. These starting materials are more readily accessible than the previously used 1,3-propanediol which is obtained enzymatically from glycerol or through hydration of acrolein with subsequent hydrogenation of the hydroxy propionaldehyde (see for example EP-B 0 412 337). Accordingly, by using 3-hydroxy propionaldehyde as the $C_3$ starting material in the process according to the invention, one oxidation equivalent less is required than for the oxidation of 1, 3-propanediol. 3-Hydroxy propionic acid as the $C_3$ starting material is obtained in simple manner through the acid-catalyzed hydration of acrylic acid. 3-Hydroxy propionic acid or a water-soluble salt thereof can also be obtained as a readily isolatable intermediate product in the catalytic oxidation of 3-hydroxy propionaldehyde to malonic acid.

The catalytic oxidation is catalyzed by a precious metal from the platinum group, thus Ru, Rh, Pd, Os, Ir and Pt. Preferred catalysts comprise palladium or platinum. These can be pure metal catalysts or supported catalysts. Supported catalysts comprising palladium and platinum are preferred. As the supporting material there can be mentioned in particular suitable activated charcoal as well as oxidic and silicatic materials.

A characteristic feature according to the invention is the quantity of catalyst to be used in the catalytic oxidation. It was found that by increasing the quantity of the precious metal—the reference quantity is herein always the quantity of precious metal—the yield increases sharply and, consequently, malonic acid can be obtained in nearly quantitative yields. The catalyst is conveniently used in a quantity corresponding to at least 10 percent by weight of the precious metal, relative to the $C_3$ starting material. Preferred is the use of a quantity of at least 20 percent by weight of the precious metal relative to the $C_3$ starting material.

The catalytic oxidation can be carried out using a suspension catalyst in a suspension reactor or using a fixed-bed catalyst in a fixed-bed reactor. If the catalyst, preferably a supported catalyst, is disposed in a fixed-bed reactor, the latter can be operated in a trickle-bed procedure as well as also in a liquid-phase procedure. In the trickle-bed procedure the aqueous phase comprising the $C_3$ starting material, as well as the oxidation products of the same and means for the adjustment of the pH-value, and oxygen or an oxygen-containing gas can be conducted in parallel flow or counterflow. In the liquid-phase procedure the liquid phase and the gas phase are conveniently conducted in parallel flow. While in the trickle-bed procedure a sufficiently large interfacial area between the liquid phase and the gas phase results automatically, in the case of the liquid-phase procedure as well as in the oxidation in a suspension reactor good dispersion of the oxygen or the oxygen-containing gas in the liquid phase must be ensured.

Since according to the invention the catalyst is to be used in as large a quantity as possible relative to the $C_3$ starting material, oxidation using a fixed-bed reactor is especially advantageous. In this embodiment the required weight ratio is attained quasi-automatically. The reaction mixture can be conducted once or several times over the fixed-bed reactor so that the pH-value can in each case be adapted outside of the reactor.

The $C_3$ starting material is supplied to the oxidation reaction in the aqueous phase. The concentration of the $C_3$ starting material in the aqueous phase is conveniently in the range between 1 and 30 percent by weight, preferably between 1 and 10 percent by weight. When using 3-hydroxy propionaldehyde as the $C_3$ starting material, it can be used as an aqueous solution with a content between approximately 5 and 20 percent by weight such as is readily obtained through the acid-catalyzed hydration of acrolein directly or after dilution with water with the subsequent separation of the non-converted acrolein.

In order to achieve a sufficiently short reaction time, the conversion is carried out at a pH-value equal or greater than 6, preferably at least 7, and in particular between 7.5 and 9. According to a preferred embodiment, during the oxidation reaction the pH-value is kept constant, preferably at a pH-value in the range between 7.5 and 9, by adding a base.

As the base there is preferably used a 10 to 50 percent by weight aqueous alkaline or alkaline earth hydroxide solution.

The oxidation is usefully carried out at a temperature of at least 10° C. and maximally 70° C. A preferred temperature range is between 20° and 60° C., in particular between 40° and 60° C. At a temperature above 70° C., 3-hydroxy propionaldehyde has low stability and, in addition, discoloration occurs.

The throughflow of oxygen is not limited. In the suspension method it is important that the liquid and the gaseous phase are brought into contact by stirring vigorously. The conversion is not very pressure-dependent so that it is usefully carried out under autogenous or slightly increased pressure, for example up to 3 bars.

Malonic acid can be obtained in a manner known per se from the malonic acid ester contained at the termination of the oxidation reaction in the aqueous phase. For example, it can be obtained through the conversion with sulfuric acid and extraction of the malonic acid or through treatment of the reaction solution with an acidic ion exchanger.

As is clearly evident from the following Examples and Comparison Examples, by using the quantity of catalyst as specified it is possible to obtain malonic acid in nearly quantitative yields in a significantly shorter time than has been possible with the quantity of catalyst conventionally used previously.

EXAMPLES

The following examples and comparison example were all carried out in a 1 l mixing flask. Exposure to oxygen introduced at 30 l/h via a glass frit took place. The reaction temperature was 50° C. To adjust the pH-value, sodium hydroxide was used. As the catalyst in all Examples and Comparison Examples 3% Pd/activated charcoal (E 105 XR/W 3%, Degussa AG) was used.

The product composition was analyzed by means of HPLC. For the separation, two amino columns SEPIL by Jasco connected in series were used. As the elution agent a mixture of acetonitrile and 0.03 molar $KH_2PO_4$ solution at a ratio of 6 to 4 was used. The column temperature was 35° C., the flow rate was 1 ml/min.

Comparison Example 1

6.5 g of catalyst were stirred in 400 ml water. The suspension was exposed to nitrogen for 24 h in order to displace the adhering oxygen (adaptation phase). To the suspension were subsequently added 90 g of a 10% solution of hydroxy propionaldehyde and the temperature was increased to 50° C. while nitrogen was introduced. The gas stream was subsequently switched to oxygen and the pH-value was increased to 11 by means of sodium hydroxide. After 1 h the 3-hydroxy propionaldehyde (subsequently abbreviated HPA) was completely converted with the solution assuming a brown color. The malonic acid fraction was below the analytical limit of detection (>2%) of the HPLC analysis.

Comparison Example 2

Comparison Example 1 was repeated, however, the pH-value was raised to 8 instead to 11. After 6 h the HPA conversion was 63.8%, however, here also the malonic acid fraction was below the analytical limit of detection of 2%.

Comparison Example 3

7.4 g of catalyst were stirred in 400 ml water. To the suspension were added 90 g of a 10 percent by weight HPA solution and the temperature was raised to 50° C. while oxygen was introduced (without adaptation phase). Therein enough sodium hydroxide was added for the pH-value to remain constant at 8. Exposure to oxygen took place with the oxygen introduced at a rate of 30 l/h and the oxidation proceeded for 11.5 h and the product mixture was subsequently analyzed. The HPA conversion was 92.9%, the malonic acid content was below the analytical limit of detection of 2%.

Comparison Example 4

Comparison Example 3 was repeated, however, the oxidation was carried out for 21 h instead of 11.5 h. According to the analysis the HPA conversion was 99% and the yield of malonic acid was 8.6%.

The Comparison Examples 1 and 2 show that through the procedure described in DE-A 41 07 986 using 3-hydroxy propionaldehyde instead of 1,3-propanediol, no malonic acid is produced. The comparison shows furthermore that high pH-values are unfavorable for the conversion of the hydroxy propionaldehyde since discoloration occurs. The Comparison Examples 3 and 4 show that after long reaction times malonic acid can be demonstrated in the product mixture; an adaptation phase appears superfluous.

Example 1

100 g of catalyst were stirred in 500 ml water. To the suspension were subsequently added 90 g of a 10 percent by weight solution of hydroxy propionaldehyde and the temperature was raised to 50° C. while the mixture was exposed to oxygen (without adaptation phase). Enough sodium hydroxide was added for the pH-value to remain constant at 8. Oxidation took place for 11.5 h at a rate of introduction of the oxygen of 30 l/h.

Analysis of the product mixture resulted in a quantitative HPA conversion and a yield of malonic acid of 96.7%.

Example 2

100 g of catalyst were stirred in 500 ml water. To the suspension were subsequently added 90 g of a 10 percent hydroxy propionic acid solution and the temperature was raised to 50° C. while the mixture was being exposed to oxygen. Enough sodium hydroxide was added for the pH-value to remain constant at 8. Exposure to oxygen (30 l/h), temperature and pH-value were maintained for 10.5 h. The product mixture was subsequently analyzed.

The conversion of hydroxy propionic acid was 97%, the yield of malonic acid was 95.4%.

What is claimed is:

1. In a process for the production of malonic acid or a salt thereof comprising the catalytic oxidation of a $C_3$ starting material with oxygen or an oxygen-containing gas in the presence of a catalyst comprising a precious metal from the platinum group in the aqueous phase at a pH-value equal to or greater than 6 and isolation of the malonic acid or a salt of the same from the reaction mixture, the improvement wherein as the $C_3$ starting material there is used 3-hydroxy propionaldehyde and the catalyst is used in a quantity corresponding to at least 10 percent by weight of the precious metal relative to the $C_3$ starting material.

2. A process as claimed in claim 1, wherein the catalyst is used in a quantity corresponding to 20 to 50 percent by weight relative to the $C_3$ starting material.

3. A process as claimed in claim 1, wherein
as the catalyst a supported catalyst is used comprising palladium or platinum.

4. A process as claimed in claim 2, wherein
as the catalyst a supported catalyst is used comprising palladium or platinum.

5. A process as claimed in claim 3, wherein
the catalyst is disposed in a fixed-bed reactor and the latter is operated
  (i) in a trickle-bed procedure wherein the aqueous phase and oxygen or an oxygen-containing gas are conducted in parallel flow or counterflow, or
  (ii) in a liquid-phase procedure with the liquid phase and the gas being conducted in parallel flow.

6. A process as claimed in claim 4, wherein
the catalyst is disposed in a fixed-bed reactor and the latter is operated
  (i) in a trickle-bed procedure wherein the aqueous phase and oxygen or an oxygen-containing gas are conducted in parallel flow or counterflow, or
  (ii) in a liquid-phase procedure with the liquid phase and the gas being conducted in parallel flow.

7. A process as claimed in claim 1, wherein
the oxidation is carried out at a pH-value of at least 7.

8. A process according to claim 7 wherein the pH value is between 7.5 and 9.

9. A process as claimed in claim 2, wherein
the oxidation is carried out at a pH-value of at least 7.

10. A process according to claim 9 wherein the pH is between 7.5 and 9.

11. A process as claimed in claim 1, wherein
the oxidation is carried out at a temperature in the range of 20° to 60° C.

12. A process as claimed in claim 2, wherein
the oxidation is carried out at a temperature in the range of 20° to 60° C.

* * * * *